US007869857B2

(12) United States Patent
Satragno et al.

(10) Patent No.: US 7,869,857 B2
(45) Date of Patent: Jan. 11, 2011

(54) COMBINATION MAGNETIC RESONANCE IMAGING APPARATUS AND PATIENT TABLE

(75) Inventors: Luigi Satragno, Genoa (IT); Orfeo Contrada, Genoa (IT)

(73) Assignee: Esaote S.p.A., Milan (IT)

( * ) Notice: Subject to any disclaimer, the term of this patent is extended or adjusted under 35 U.S.C. 154(b) by 722 days.

(21) Appl. No.: 10/716,402

(22) Filed: Nov. 20, 2003

(65) Prior Publication Data
US 2004/0162480 A1 Aug. 19, 2004

(30) Foreign Application Priority Data
Nov. 28, 2002 (IT) ................................ SV02A0057

(51) Int. Cl.
*A61B 5/05* (2006.01)
(52) U.S. Cl. ...................... 600/415; 600/410; 600/421; 5/601
(58) Field of Classification Search ................. 600/410, 600/407, 415, 421; 324/318, 307, 312–314, 324/259; 128/653; 348/11, 17, 20, 39; 5/601
See application file for complete search history.

(56) References Cited
U.S. PATENT DOCUMENTS
5,623,927 A 4/1997 Damadian et al.

| 6,029,081 | A | * | 2/2000 | DeMeester et al. | ........... 600/410 |
| 6,445,185 | B1 | | 9/2002 | Damadian et al. | |
| 6,801,038 | B2 | * | 10/2004 | Carrozzi et al. | ............. 324/318 |
| 2002/0057088 | A1 | | 5/2002 | Carrozzi et al. | |
| 2002/0123681 | A1 | * | 9/2002 | Zuk et al. | .................... 600/410 |
| 2002/0173715 | A1 | * | 11/2002 | Kruger et al. | ................ 600/410 |

FOREIGN PATENT DOCUMENTS

| DE | 19853463 A | | 5/2000 |
| DE | 19923947 A | | 12/2000 |
| EP | 0995397 A | | 4/2000 |
| EP | 1004269 A | | 5/2000 |
| IT | 1 004 269 A1 | * | 5/2000 |
| JP | 11028199 | * | 2/1990 |

* cited by examiner

*Primary Examiner*—Brian Casler
*Assistant Examiner*—Joel M Lamprecht
(74) *Attorney, Agent, or Firm*—Buchanan Ingersoll & Rooney PC

(57) ABSTRACT

A combination Magnetic Resonance imaging apparatus and patient table, which apparatus has a magnet structure, defining a cavity for accommodating a part of the body under examination, which is supported by a base block, the patient table and the apparatus having a base block and a supporting structure respectively, that are slidable in at least one, or more directions. The patient table and the Magnetic Resonance imaging apparatus have a mechanism for removable connection therebetween and guide thereof along predetermined relative displacement paths.

34 Claims, 9 Drawing Sheets

COMBINATION MAGNETIC RESONANCE IMAGING APPARATUS AND PATIENT TABLE

The present application claims priority to Italian Application No. SV2002A000057 filed Nov. 28, 2002, the entire disclosure of which is herein expressly incorporated by reference.

BACKGROUND

The present invention relates to a combination Magnetic Resonance imaging apparatus and patient table, which apparatus has a magnet structure, a cavity for accommodating a part of the body under examination, which is supported by a base block. The patient table and the apparatus have a base block and a supporting structure respectively, that are slidable in at least one, and possibly more directions.

Such combinations are used in prior art and are provided in a number of different variants. Typically, a Magnetic Resonance imaging apparatus, including at least the magnet structure for exciting and receiving Magnetic Resonance signals, is fitted on a carriage whereto the magnetic structure is linked by combinations of arms, saddles, carriages, joints and rotary supports to allow the magnetic structure to be positioned coincident with the anatomic regions of the patient, who lies on a reclining chair, table/chair or table.

These constructions are suitable for apparatuses having very small and light magnet structures, and not for medium-range apparatuses, with magnet structures sized in an intermediate range between total body structures (i.e. delimiting cavities which can contain a considerable portion of the patient body, or the whole body), and miniature structures designed for specific diagnostic or therapeutic applications.

While for small apparatuses the combination with the patient table is not so important in terms of the overall size of the apparatus and table assembly, as the main purpose of these apparatuses is to be combined with any type of table, table/chair or chair, and to allow displacement of the apparatus from one patient to another, e.g. to their respective hospital or treatment beds, in intermediate range apparatuses, the integration with the table is of the utmost importance, as these apparatuses still have a relatively large size, even though they are smaller than total body apparatuses. As the number of these apparatuses increases in health facilities, it is increasingly difficult to find sufficient spaces for them, and there exists the need of apparatus and table combinations, that are widely adaptable to the size and shape of premises, to allow full use of the apparatus potential even in rooms that are not much larger than the plan size of the apparatus or have an ineffectively distributed plan surface.

Also, for a better design of premises in new health facilities, due to the influence of building costs per cubic meter a higher versatility is also advantageous when the building is still to be designed and built and allows the use of premises or rooms with unfavorable plan shapes to contain Magnetic Resonance imaging apparatuses.

Special apparatus constructions may be provided in response to various space requirements of health facilities. Nevertheless, these constructions are hardly or only partly obtainable by using industrial mass-production processes, and this involves an increase of fabrication costs and times. In fact, it is apparent that apparatuses with larger layouts require a greater number of specially designed parts or parts to be kept in stock, which involves a time and cost increase.

SUMMARY

Exemplary embodiments of the present invention are directed to the problem of providing a combination comprising a Magnetic Resonance imaging apparatus and at least one patient table, which can effectively obviate the above drawbacks, while providing the highest design versatility to meet a great number of location needs, while minimizing the need of having a great number of construction parts, and limiting adaptability costs, without restricting the operating potential of the apparatus.

Exemplary embodiments of the present invention achieve the above purposes by providing a combination as described hereinbefore, in which the table and the Magnetic Resonance imaging apparatus have means for removable connection therebetween and guide thereof along predetermined relative displacement paths.

According to a variant, the combination may include two or more patient tables, that can be simultaneously coupled to the Magnetic Resonance imaging apparatus, in different positions relative thereto.

The means for coupling patient tables to the Magnetic Resonance imaging apparatus advantageously are guide means for displacement of tables relative to each other and to the Magnetic Resonance imaging apparatus.

Particularly, these guide and coupling means consist of an arched, preferably circular guide and of a carriage to be removably coupled thereto, the guide being associated to the Magnetic Resonance imaging apparatus, and each table being associated to a carriage that can be coupled to said guide, whereas the table(s) have a supporting structure with wheels or rollers sliding along the bearing surface, i.e. the floor or a base block.

The base block of the Magnetic Resonance imaging apparatus may have wheels, rollers or other means for sliding relative to the bearing surface, i.e. the floor or a support platform.

Particularly, a platform may be also interposed between the Magnetic Resonance imaging apparatus and the floor. The platform is composed of a base plate and an upper Magnetic Resonance imaging apparatus supporting plate. The upper support plate lies over the base plate, a sliding guide being interposed between said two plates, which guide is parallel to the table sliding guide, associated to the Magnetic Resonance imaging apparatus.

According to an advantageous characteristic, the table sliding guide associated to the Magnetic Resonance imaging apparatus and the sliding guide interposed between the base plate and the upper plate of the platform are oriented along at least one straight axis.

In a particular advantageous embodiment, the Magnetic Resonance imaging apparatus is associated to a table sliding guide that has the shape of a sector of a circle, whose axis is oriented perpendicular to the floor or to the apparatus supporting surface.

The sliding guide between the base plate and the upper supporting plate of the platform for the Magnetic Resonance imaging apparatus also has the shape of a sector of a circle and is coaxial to the table sliding guide associated to the Magnetic Resonance imaging apparatus.

The platform may be of any shape but, when it is combined with a table sliding guide having the shape of a sector of a circle, the platform advantageously has an annular or disk- or plate-like shape. This platform may extend over a limited section, corresponding to the surface supporting the base block of the Magnetic Resonance imaging apparatus, along the table sliding guide. In this case, the opposite side(s) of the Magnetic Resonance imaging apparatus have slidable support elements whose height compensates for the height difference of the platform, which elements rest directly on the platform bearing floor, whereas the table supporting structure lies directly on the platform bearing floor, which table supporting structure has elements for sliding on the floor.

In one variant, the platform also partly extends beneath the table(s), coincident with at least the portion of the table supporting structure at the side whereat the table(s) are coupled to the Magnetic Resonance imaging apparatus sliding guide. In this case, the table structure rests on the platform at one end side and directly on the floor at the other end aide. Obviously, the platform which supports at least a portion of the table supporting structure may be also displaced parallel to the apparatus supporting platform. Particularly, if a guide is provided for slidable displacement of table(s) relative to the apparatus or vice versa, the two platforms are rotatable, particularly coaxial to each other and to the sliding guide between the table(s) and the apparatus.

The above description clearly shows that, by using a limited combination of parts, i.e. wheels, guides, carriages and/or translating and/or rotating platforms, a wide range of designs may be obtained which allow, as described hereafter in greater detail, the location of the apparatus in premises of different sizes and plan shapes.

It will be apparent from the following description that the above results may be reached by using a very small number of modular parts, which allow a versatile combination between the apparatus and the table(s).

Particularly, a modular construction allows replacement of, in any instance, a few limited parts to adapt the apparatus to new space requirements of premises, when apparatuses are to be moved from one room to another, without requiring important changes, except the disassembly of some parts and the addition of other parts, when needed.

The main designs of the combination, particularly suited to the most frequent assembly situations or conditions, as well as a particularly advantageous embodiment of the MRI apparatus and table(s) combination, are described hereafter in greater detail.

BRIEF DESCRIPTION OF THE DRAWINGS

The characteristics of the invention and the advantages derived therefrom will appear more clearly from the following description of a few non limiting embodiments, illustrated in the annexed drawings, in which.

DETAILED DESCRIPTION

The embodiments as shown in the figures particularly relate to a combination of a patient table according to the invention with a Magnetic Resonance imaging apparatus. This combination shall not be intended to restrict the inventive scope. In fact, instead of the lower horizontal side 201 of the magnet cavity, which side 201 complements the table recess 302, working or operating surfaces, or sides for delimiting operating spaces of any type and/or any diagnostic and/or therapeutic equipment may be provided to complement the recess 302.

Since in Magnetic Resonance imaging apparatuses cost reduction and size reduction are critical problems, still in direct connection with each other, the combination as shown and described herein is composed of a patient table and a Magnetic Resonance imaging apparatus, particularly a low to medium or high to medium cost apparatus, having a small to medium size. For these ranges of products, the described embodiment allows the highest design versatility with a minimum number of design-specific parts, thereby obtaining such versatility at limited costs. Also, the examination features of apparatuses are enhanced, whereas sizes are reduced.

With reference to FIGS. 1 to 7, a Magnetic Resonance imaging apparatus has a magnet part 1. The magnet as shown in the figures has a C or U shape, defining a cavity that is open on three peripheral sides, and is delimited by an upper side 101, a lower side 201 and a vertical side 301. These three sides are made of the same material as the envelope covering the magnetic structure and other operating equipment, e.g. plastic or the like, which envelope has a recess 401 in a predetermined position, for receiving a receiving coil holder (not shown in detail).

The free ends of the upper and lower sides 101 and 201 are rounded, preferably with a semicircular profile. A patient table 2 is associated to the magnet 1. The patient table is composed of two parts 102, 202. The part 102 has a support surface with a hollow 302 that is complementary in shape and corresponding in size to the lower side 201 of the magnet 1, whereas its outer side may be shaped in any manner, preferably like a circular segment with an angular extension above 180°, such as to fully surround the central U-shaped hollow. The table part 102 is designed to be slid around the side 201 of the magnet 1 which complements the support surface. The table part 102 is supported by at least two wheeled 4 legs 3, which are provided at least at the end side for connection with the other table part 202, itself being supported by two wheeled 4 legs 3, provided on the free end side opposite to the one for connection with the part 102. The supporting surface of the two table parts is level with the side 201 of the magnet 1. The table part 202, named "outer part" in the description and claims, rests, at the end for connection to the part 102, on a guide 5, which is supported in a cantilever arrangement in a downward direction and towards the connection end of the table part 202 by vertical pins 6 and radial pins 7, disposed radially inwards with respect to the guide. The guide 5 is advantageously made of an arched cylindrical metal section, whose arched profile corresponds to the outer circular profile of the table part 102. The table part 102 has a case 402 to cover the supporting legs and other equipment, which case is superimposed to the case 501 of the apparatus in the assembled condition, thereby providing a particularly aesthetic seamless aspect to the apparatus. Thanks to this design, the table 2 may be coupled to the magnet 1, thereby forming a complete patient supporting surface, having such a size as to conveniently support the patient body, while reducing the overall size, i.e. the projecting extension of the patient table with respect to the magnet. Moreover, the so-called outer part 202 of the table may rotate around the part 102, which is coupled to and complemented by the lower side 201 of the magnet 1, in such a manner as to have any orientation whatever in the horizontal plane with respect to the part 102. In this case, the C or U shape of the magnet provides an angular orientation range of about 180°, thereby allowing disposition of the patient either along an axis parallel to the vertical side 301 or along an axis perpendicular to said side or along axes having intermediate directions on either side of the axis perpendicular to the vertical side 301.

In combination with apparatuses having magnets of different shapes, the rotation of the part 202 relative to the part 102 may be either further restricted, e.g. by using magnets having two perpendicular open sides, or extended, e.g. by using magnets in which the cavity is only defined by two sides, e.g. the upper horizontal side and the lower horizontal side, whereas the pole pieces associated to said two sides are kept at a distance by posts or columns, whose number may vary from 1 to 2, 3 or more elements. The above construction may be obviously also associated with magnets having a cavity that is only open on two opposite sides, i.e. to annular magnets. Here, a sector-shaped section of a sliding guide 5 may be provided in the area or on each open side of the magnet.

In order that the above table may be used, for instance, to transport the patient, the part 102 may also have a pair of wheeled legs at the ends of the stems of the U shape. Further, a removable element may be provided to close the hollow and complement the support surface, e.g. by using slidable engagement means.

With particular reference to FIGS. 3 to 7, the table part 102 may be slidably coupled to the magnet 1. This may be obtained thanks to guide means, some of them being associated to the sides of the magnet 1, the stems of the supporting surface with the U-shaped hollow being superimposed thereto.

The above may be obtained in any manner. In the embodiment as shown in the figures, a preferably cylindrical guide rod 10 is associated to each stem of the U-shaped hollow 302 of the table part 102, said rod engaging a sliding guide consisting of rollers that are vertically opposed and spaced at a distance corresponding to the thickness of the guide rod 10.

Particularly, the guide rod is engaged between two lower rollers 11 and one upper roller 12. All the rollers have a peripheral annular groove having a semicircular or substantially semicircular shape, whereby the cylindrical guide rod is also held to a certain extent in a horizontal transverse direction. The upper roller 12 is preferably supported in such a manner as to yield against a predetermined elastic compression force exerted toward the two opposite rollers 11. This is obtained by means of a swinging arm 112 which is pivoted about an axis parallel to that of the roller 12, whereas said roller is mounted on one end of the arm, the other end being linked to a spring that is secured to the supporting structure of the apparatus. Also, the guide rod may have radial recesses, such as annular grooves or ridges which define, in combination with the elastically supported roller 12, predetermined positions that may be easily passed through by exerting a certain pushing or pulling force. In combination with the above, the guide rods 10 and/or other parts of the apparatus 1 and/or of the table part 102 may have sprung and/or shock-absorbing abutments.

The table part 202 is engaged on the arched guide 5 by means of a carriage 15 which is provided at the end side of the part 202 facing toward the part 102. The carriage 15 has two upper wheels 16 and two opposed lower wheels which are supported with their axes oriented radially with respect to the arched guide and, like the rollers 11 and 12, have peripheral grooves whose transverse shape is substantially semicircular or similar. The arched guide 5 also has preferably, but without limitation, a circular profile. The arched guide 5 is supported in a cantilever fashion downwards and radially out of the supporting surface of the table part 102 by vertical pins 6 that are arranged along the extension of the guide 5, and whose lower ends are linked to the arched guide 5 by means of radial fingers 7. The vertical pins 6 may be arranged in any manner along the arched guide 5, for instance in an equally spaced arrangement, or in such a manner as to form location marks for certain predetermined orientations of the so-called outer part 202 of the table, relative to the part 102, which is coupled to the side 201 of the magnet 1. In an intermediate position between the upper and the lower wheels a member 18 is provided for grasping the vertical pins 6, which act as abutments for stopping the table part 202 in a predetermined angular position. The gripping member 18 consists of a plate having a central U-shaped hollow 118, for engagement of the vertical stop pins 6. The gripping plate 18 is supported on a lever or fork 19, which is supported in such a manner as to oscillate about a horizontal axis 20, transverse to the longitudinal axis of the table part 202. Two elastic members, e.g. two helical springs inserted at the ends of the axis 20 and connected by one of their ends to said axis 20 and by the other end to a stationary abutment of the structure of the table 202, permanently stress the lever or fork 19 to cause it to bring the gripping plate 18 to a horizontal position, in which the latter extends in a radial position, engaging the vertical stop pins 6. A tie rod 23, linked to the lever or fork 19 is connected to a manual release lever 24 at the free end of the table part 202. By moving said lever 24, the support lever or fork 19 is displaced backwards, thereby causing the gripping plate 18 to swing to a radially retracted position in which it releases the vertical stop pins 6.

According to an improvement, in order to allow a convenient automatic grasp to a vertical stop pin, a cam 25 is secured to a gripping plate 18. The latter consists of a downwardly vertically projecting plate. The plate-like cam 25 has a W shape along its lower edge, in which the outer stems are less inclined than the two inner stems. The plate-like cam 25 extends vertically downwards to come to interaction with the profile with the radial fingers 7 which form fixed abutments for controlling it. The inclined outer stems form lead-in surfaces which cooperate, while the carriage is displaced along the guide, with a corresponding radial finger 7. The cam 25 causes the gripping plate 18 to be progressively lifted to a position in which it releases the vertical pins, and passes beyond the corresponding vertical stop pin. When the radial finger 7 passes beyond the lower apex and penetrates between the two inner inclined stems of the plate-like cam 25, the gripping plate is lowered again to a position in which it engages the corresponding vertical stop pin 6 which is in the proper position to be engaged in the hollow 118. The W shape of the platelike cam allows to use said features of automatic snap engagement with the stop pins 6 for displacements in both directions.

In the embodiments of FIGS. 1 to 5, the patient table rotates around the apparatus. Particularly, in the embodiment as shown in these figures, a part 202 of the table rotates around an intermediate table part which is in turn coupled to the Magnetic Resonance imaging apparatus 1, said intermediate part 102 being able to be translated along the guides 10 along an axis perpendicular to the rear vertical wall of the magnetic structure.

Figure 11:
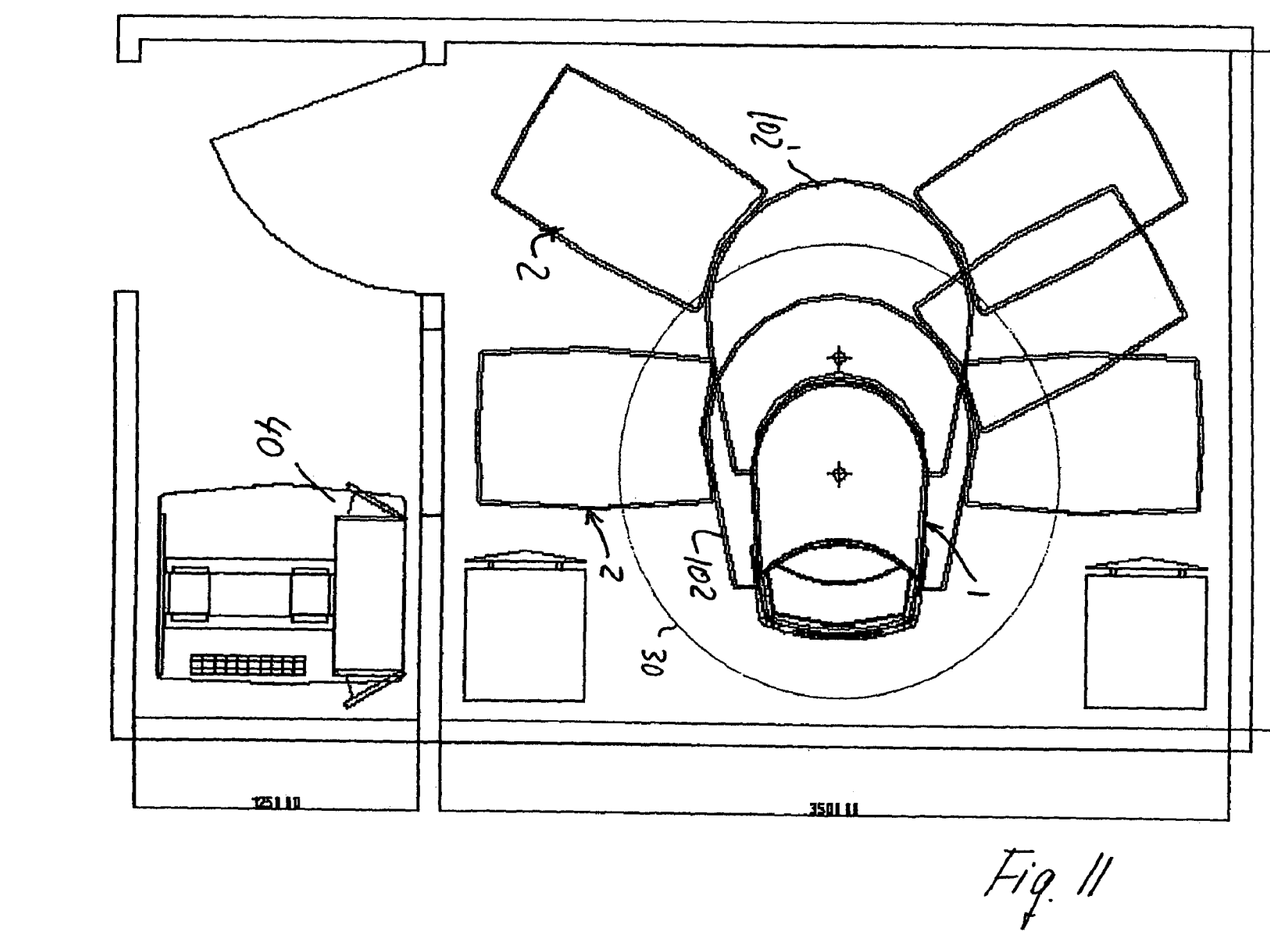
FIG. 11 shows yet another variant of the Magnetic Resonance imaging apparatus and table combination in which said apparatus is provided in combination with two diametrically opposite patient tables that are at least partly displaced angularly relative to the apparatus through a limited angle, as well as in combination with the variant providing slidable or translatable connection of the intermediate table portion with the MRI apparatus.

As shown in FIG. 11, at least two tables or two table parts 202, 202' may be coupled to the sliding guide 5 having the shape of a sector of a circle. These may be provided on substantially diametrically opposite sides. This design avoids the full rotation of the single table along the sliding guide 5, which would require a free space along the front side of the apparatus, i.e. along the open front side of the apparatus, which is at least equal to the length of the table part 202. Therefore, the two-table design allows placement of the apparatus in a room having a rectangular surface distribution, i.e. plan shape. The room would be insufficient for an apparatus associated to a single table, as this would not allow the table to swing between the two extreme, substantially diametrically opposite positions. However, the provision of two tables allows the use of the whole potential of the apparatus even in a narrow and long room. Furthermore, as is apparent from FIG. 11, the two tables may swing through a certain angular distance, whose extent depends on the room width and, in a minimal room width conditions, is certainly below 90°, between the table limit stop position and the swung position at the opposite limit stop of the sliding guide. In these conditions, instead of providing a single sliding guide 5, at least two diametrically opposite, independent and separate sliding guide sections may be provided.

For the above features and design, the sliding guide 5 or the two sections thereof may be mounted directly on the Magnetic Resonance imaging apparatus, and not on the intermediate table part 102.

Nevertheless, the presence of this intermediate part allows (as shown in FIG. 11) the two table parts 102, 202, to perform an additional translation movement, relative to the apparatus, obviously provided that the room width allows to do so.

Alternatively to or in combination with the possibility of swinging a single table or two tables along the sliding guide, the apparatus itself may be arranged to rotate about an axis coaxial to the sector-shaped sliding guide 5.

Figure 1:
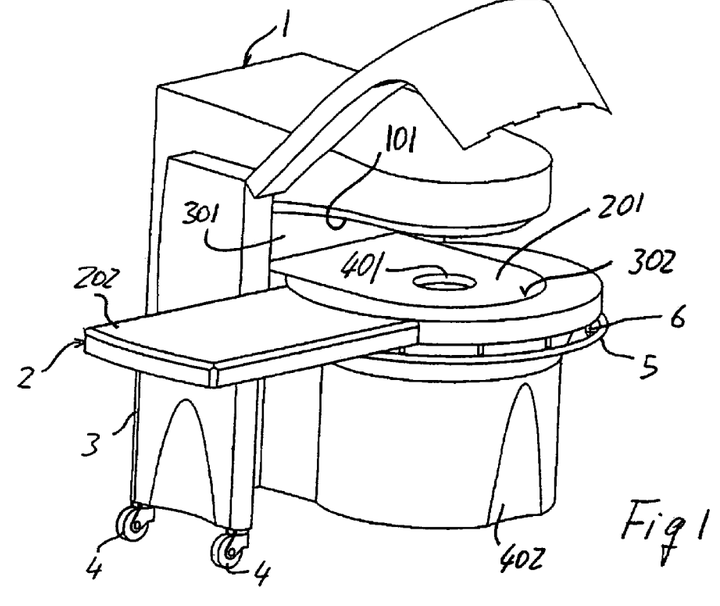
FIG. 1 is a perspective view of a Magnetic Resonance imaging apparatus having a C or U shape, and horizontal pole pieces, in combination with a patient table that is coupled to the apparatus in such a manner as to be displaceable around the lower pole piece of the magnetic structure along a guide that has the shape of a sector of a circle and extends along the peripheral edges of said lower pole piece, which delimit at the bottom the open sides of the magnetic structure, the table being oriented with its horizontal axis radial to the sliding guide shaped like a sector of a circle, and being displaced angularly with its longitudinal axis oriented parallel to the vertical closed side of the magnetic structure.
Figure 2:
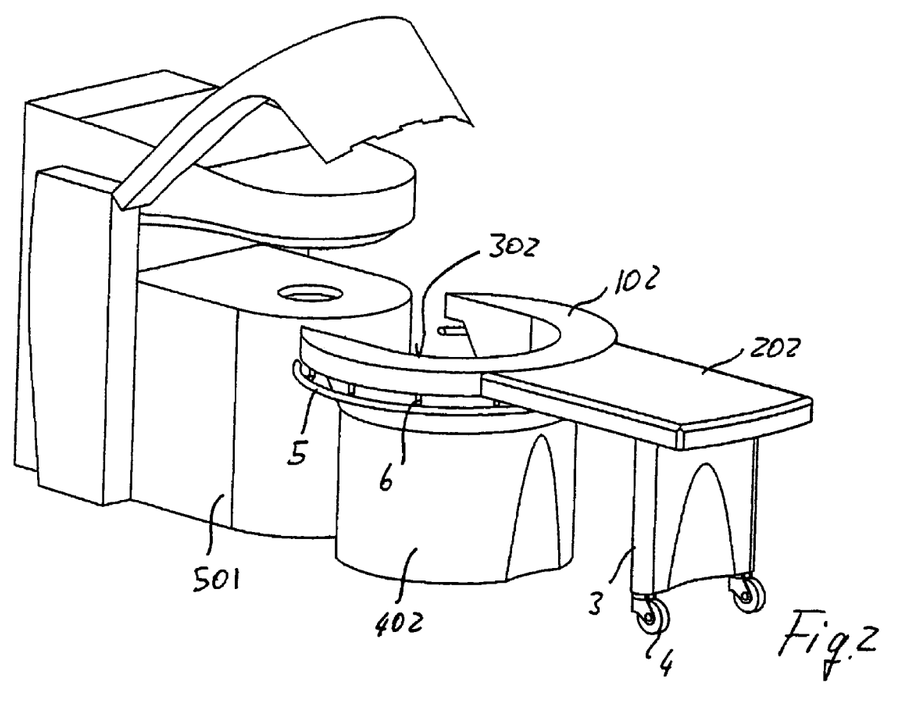
FIG. 2 is a perspective view of a variant of the first embodiment of the invention, in which the apparatus has a magnet and a table, the latter being composed of two parts that may be articulated and oriented in the horizontal plane, the table being separated from the magnet.
Figure 3:
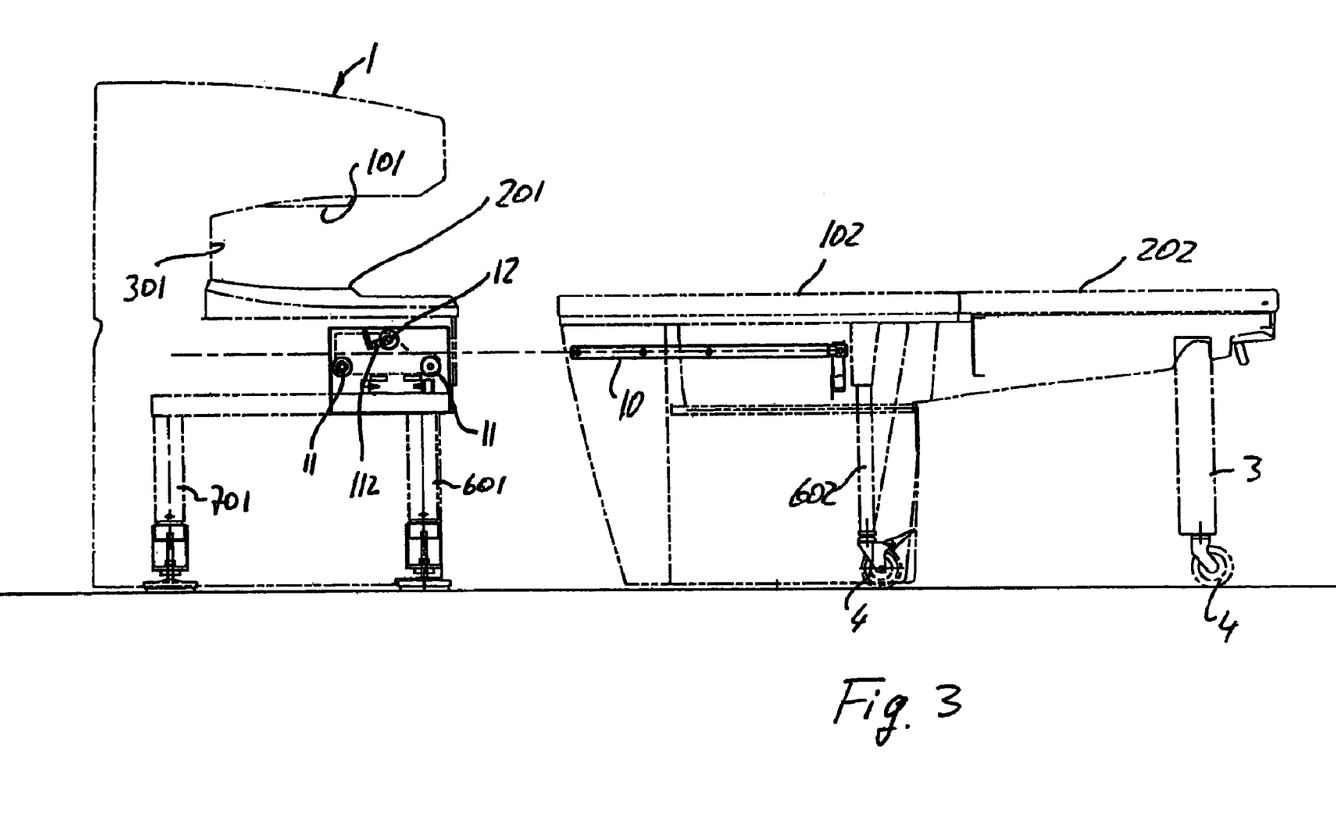
FIG. 3 is a side elevational, partly sectional view of the apparatus as shown in FIG. 2, with the table being separated from the Magnetic Resonance imaging apparatus.
Figure 4:
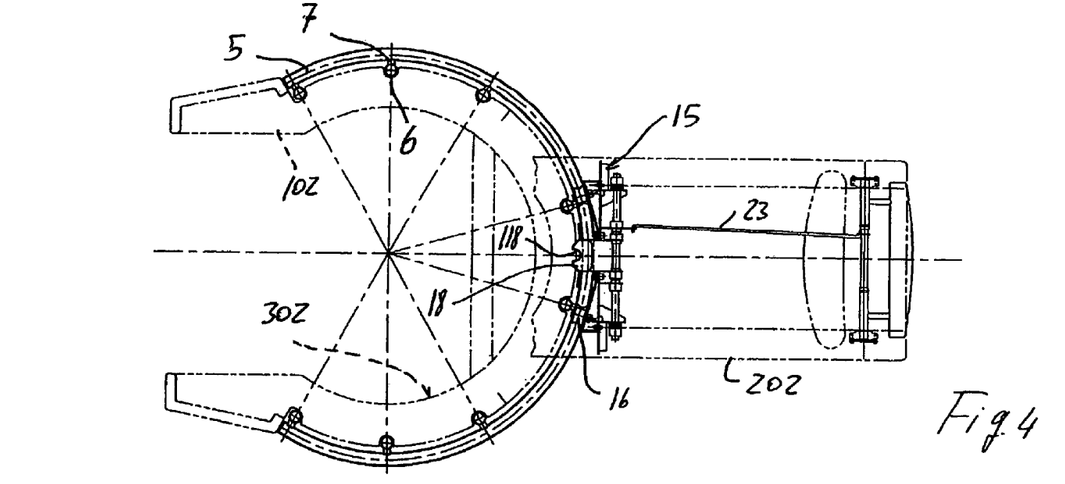
FIGS. 4 and 5 are a top plan and a side view respectively, in partial section, of the patient table as shown in the previous figures.
Figure 5:
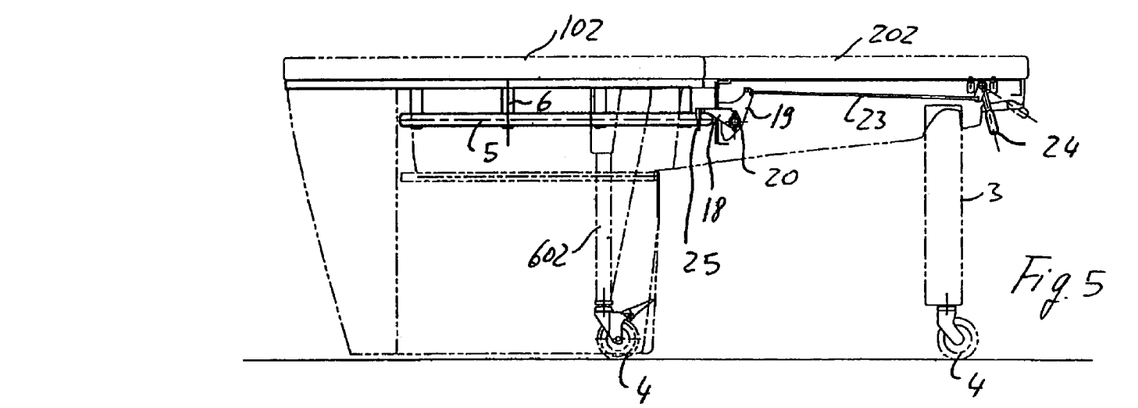
Figure 6:
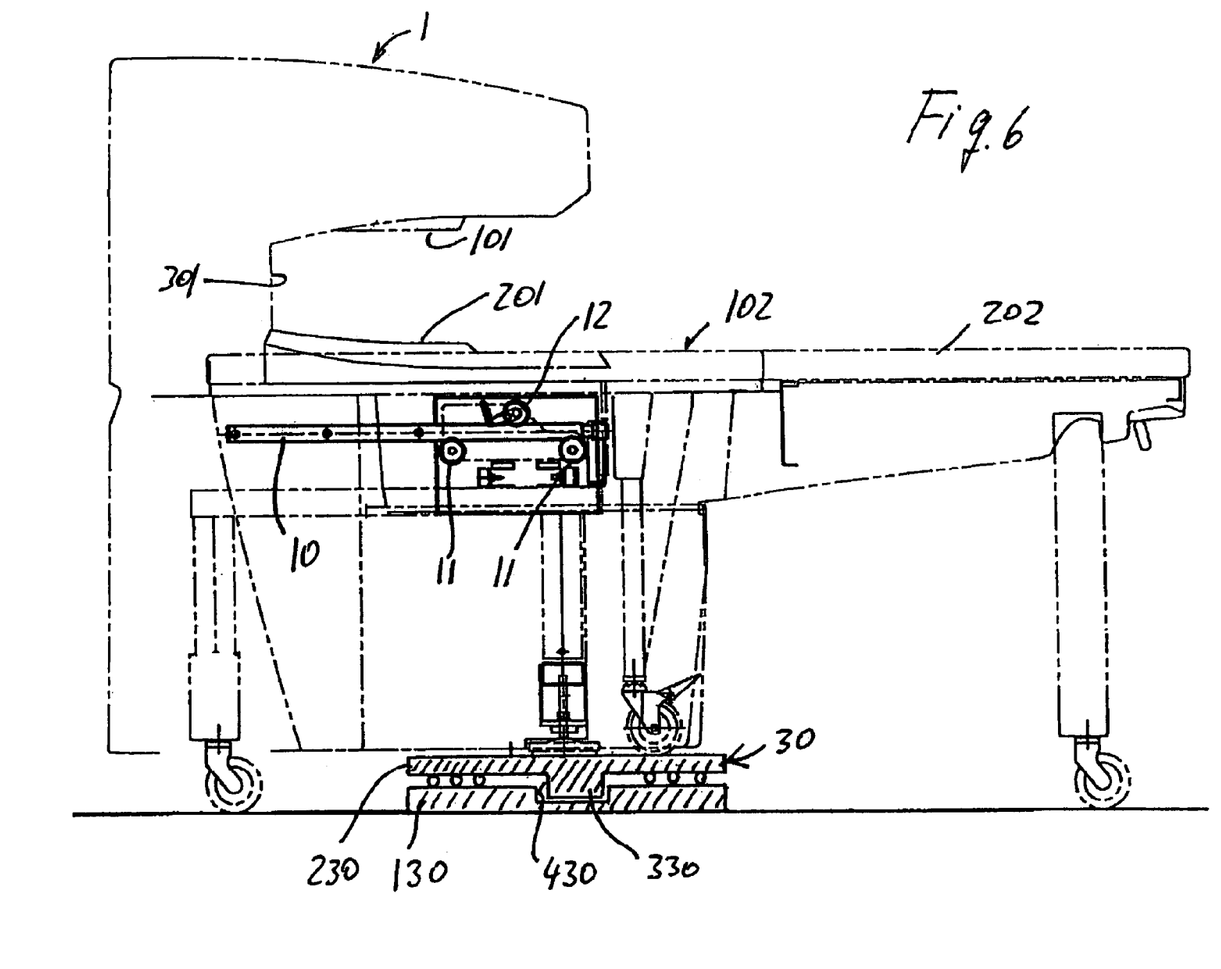
FIGS. 6 and 7 show two variants of an embodiment in which the table is not the only rotating part of the combination, and the Magnetic Resonance imaging apparatus itself rotates relative to the table and coaxial to the table sliding guide.
Figure 7:
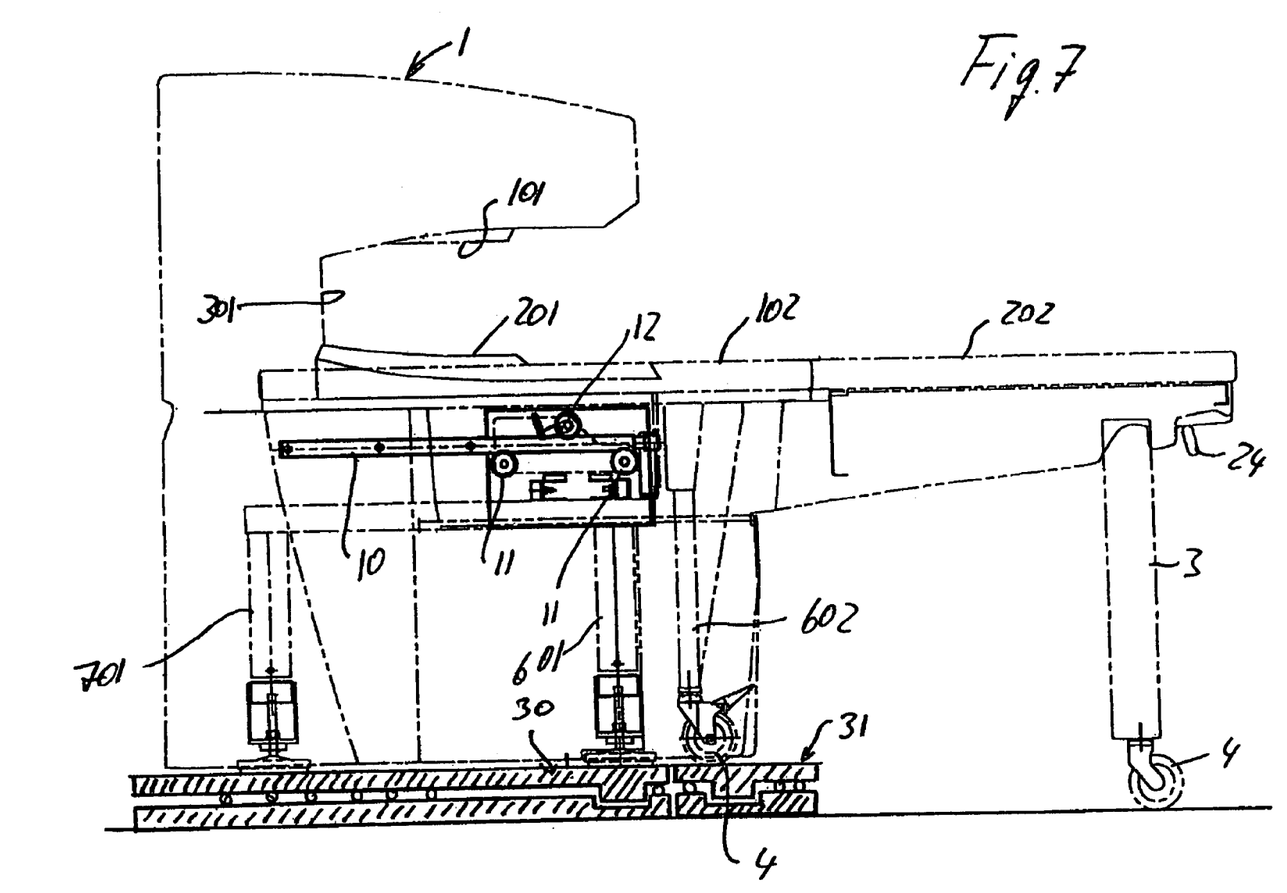

FIGS. 6 and 7 show two non-limiting embodiments of this additional characteristic. The Magnetic Resonance imaging apparatus may be rotated by providing that at least the portion of the apparatus that is coupled to the table 102, 202 be supported by a platform rotatable along an annular path, coaxial to the axis of the sliding guide 5 for the table, i.e. for the table part 202.

The platform, designated by numeral 30, may be rotated in any manner. A possible embodiment may provide a platform 30 composed of a base plate 130 and an upper apparatus supporting plate 230, rotary guide means 330, 430 being provided between the two plates along the predetermined path, as well as means allowing the two plates to slide relative to each other. As shown in the figure, the upper plate has a projection 330 which is engaged in a guide track 430, whereas one or more ball rows are provided between the two plates 130, 230.

In the embodiment of FIG. 6, the platform which is shaped, for instance, like an annular band coaxial to the table sliding guide 5, extends and is located coincident with the supporting legs at the front open side of the magnet structure, said legs resting thereon, and also supports the legs 602 of the table part 102, which may have wheels 4 at their ends to allow displacement along the annular guide 5 of the table.

However, the legs 3 of the part 202 of the table 2 lie directly on the floor, outside the rotating platform 30 and are appropriately wheeled 4. Similarly, the rear legs or supports 701 of the Magnetic Resonance imaging apparatus 1 rest on the floor and have wheels 4. As shown in the figure, the platform 30 only supports the legs of the table 102 and the legs 601 of the front side of the Magnetic Resonance imaging apparatus. Nevertheless, a single platform may be provided, which is composed of annular bands displaceable along a circular path coaxial to the table part sliding guide 5 for only supporting the legs 601 on the front side of the apparatus and the legs 602 of the non rotating part 102 of the table 2, whereas the legs 3 of the table 2 and the rear legs 701 of the apparatus rest on stationary parts of the platform.

In the variant of FIG. 7, the rotating platform 30 for supporting the Magnetic Resonance imaging apparatus and the rotating platform for supporting the legs 602 of the table part 102 or the legs of a one-piece table, disposed on the apparatus connection side are separated.

These two rotating parts 30, 31 of the platform may be shaped like annular bands extending over a certain sector of a circle, the platforms 30, 31 rotating about an axis coaxial to the axis of the 15 sliding guide 5 for the carriage 15 associated to the table 2. Alternatively to the above, as shown by way of example, the Magnetic Resonance imaging apparatus platform 30 also extends over the area of the rear legs 701 of said apparatus.

The platform may consist of a single base plate, extending both beneath the apparatus and beneath the table(s) and having different upper plate parts, in the form of separate coaxial annular bands which are slidably engaged along guides that are coaxial to the annular bands and to the axis of the sliding guide 5 for the table(s) 2.

Obviously, the above construction with reference to FIGS. 6 and 7, applies both to the single table variant and to the two-table variant as shown in FIG. 11.

If the supporting surface is composed of annular band-like parts having a circular or sector shape, with a certain radial size, a translation of the intermediate table part 102 relative to the apparatus may be provided in combination therewith. Here, the table rests on the platform with the interposition of wheels which allow a relative displacement thereof in the radial direction. The deflection from the coaxial relationship of the sliding guide 5 for the table(s) 2 to the axis of rotation of the platform is very little and is compensated by the width of the axial size of the annular bands which compose the upper supporting plate of the platform.

Figure 8:
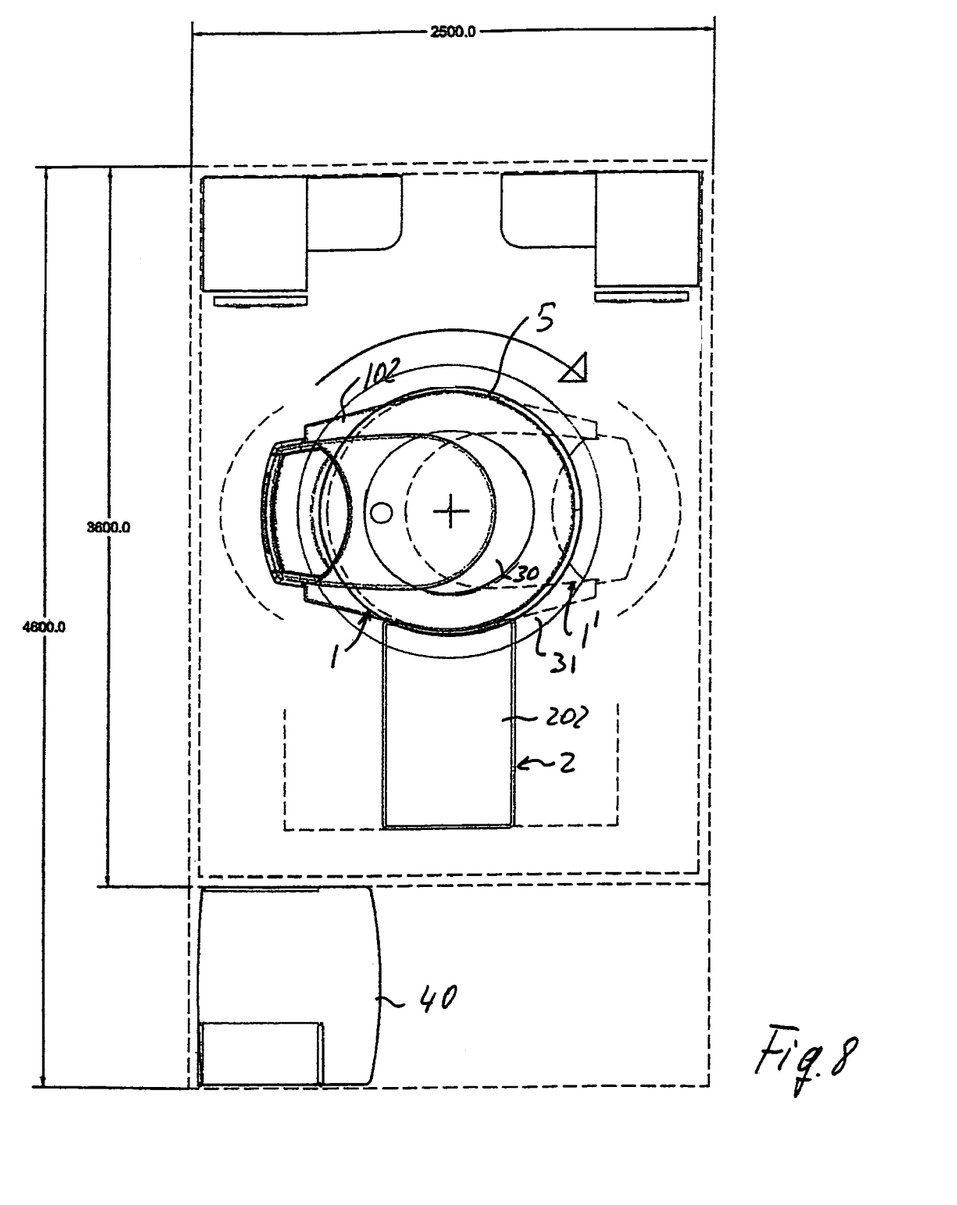
FIGS. 8 to 10 show three variant designs of the Magnetic Resonance imaging apparatus and table combination, as shown in FIGS. 6 and 7 in which the apparatus is rotated relative to the table.
Figure 9:
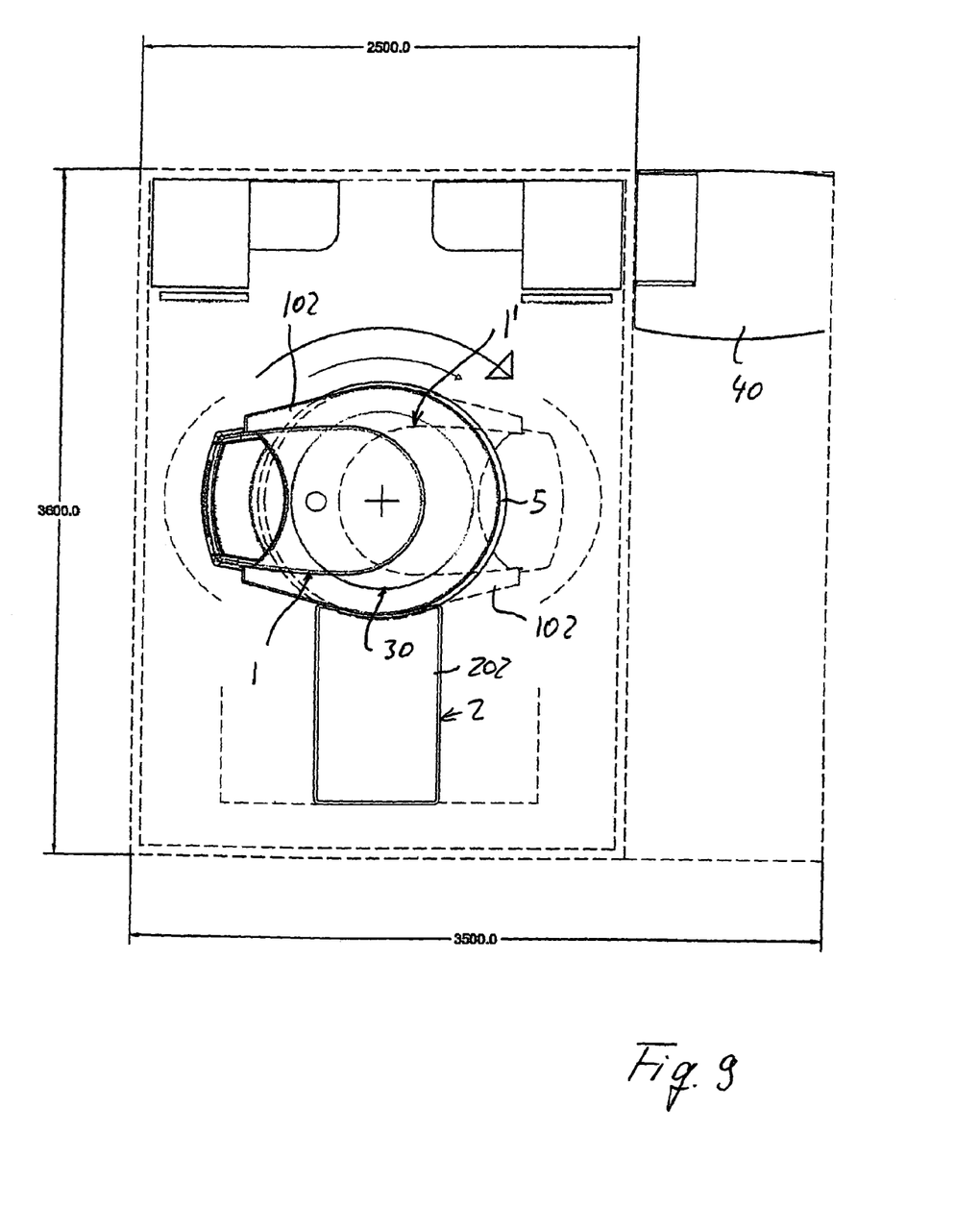
Figure 10:
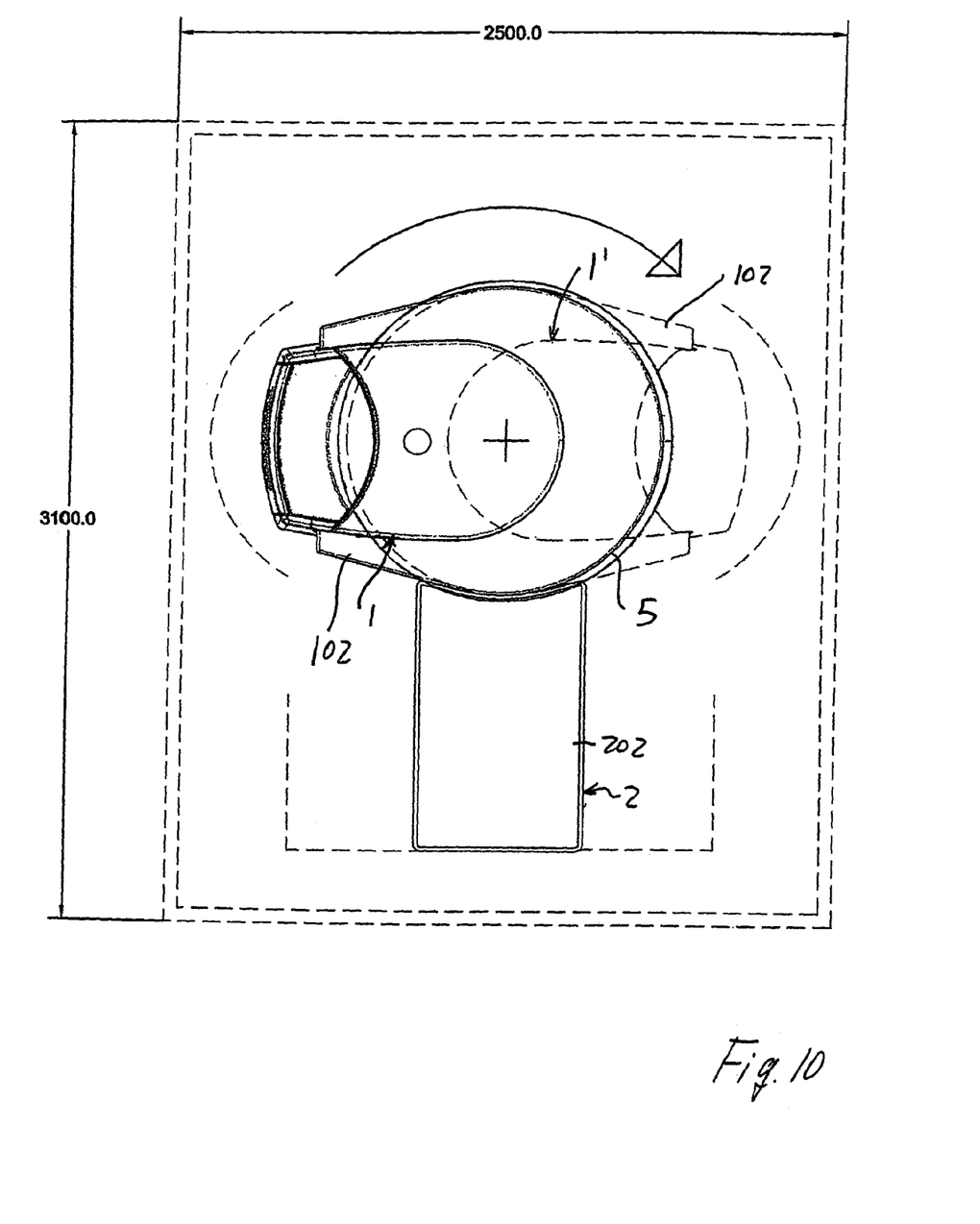

FIGS. 8 to 10 show three alternative designs for housing the combination Magnetic Resonance imaging apparatus 1 and table 2 as shown in FIGS. 6 and 7.

As shown in FIGS. 8 and 9, a separate console is provided which contains the control and monitoring electronics of the apparatus 1, which is designated with numeral 40. The table is stationary and may swing through limited paths along the sliding guide 5, whereas the apparatus rotates. In the figures, the apparatus rotates through 180°, a first extreme position being outlined in continuous lines and an opposite extreme position being outlined in dashed lines, and designated with numeral 1'. Here again it is apparent that the design of a rotating apparatus, unlike that of the table rotating around the apparatus, allows for a reduced room space requirement, without limiting the functions of the apparatus as regards its orientation relative to the table.

FIG. 10 shows a variant, in which the control and monitoring electronics is contained in the base block of the apparatus.

The rotation of the apparatus may be also implemented in a combination having, like in FIG. 11, two or more tables 2.

FIG. 8 shows a variant having two separate coaxial rotating platforms for the apparatus 1 and the intermediate table part which platforms are designated with numerals 30 and 31, like in FIG. 7, whereas FIG. 9 shows the variant of a single common rotating platform 30, as shown in FIG. 6.

Advantageously the various parts, e.g. stationary feet, wheels 4, guides, carriages and platforms may be provided as members to be coupled and uncoupled in a modular manner, in such a manner as to obtain different apparatus designed, with no excessive time and cost wastes, and with a very small number of parts in stock.

The rotation of the platform and/or the tables may be actuated either manually and by using electric and/or hydraulic motors. The vibrations may be deadened or absorbed by providing shock absorbers between the various movable parts.

The platform advantageously provides a passage for the cables connecting the apparatus 1 to the control and monitoring units 4, said passage being possibly formed in said platform and the cables coming out therefrom in the central area of the axis of rotation to avoid their involvement in the rotary motion.

The invention has been described herein with reference to particular embodiments. However, it will be readily apparent to those skilled in the art that it may be possible to embody the invention in specific forms other than those described above. This may be done without departing from the spirit of the invention. Embodiments described above are merely illustrative and should not be considered restrictive in any way. The scope of the invention is given by the appended claims, rather than the preceding description, and all variations and equivalents which fall within the range of the claims are intended to be embraced therein.

What is claimed is:

1. A system comprising:
a magnetic resonance imaging apparatus; and
a patient table,
wherein the magnetic resonance apparatus has a magnet structure defining a cavity for accommodating a part of a body under examination, which magnetic structure is supported by a magnetic structure base block,
the patient table having a supporting structure that is slidable in at least one direction, wherein the patient table and the magnetic resonance imaging apparatus have a curved connection therebetween that allows relative rotation between the patient table and the magnet structure when connected to each other,
the curved connection includes a guide for relative displacement between the patient table and the magnetic resonance imaging apparatus,
wherein the base block of the magnetic resonance imaging apparatus is disposed on a platform interposed between the magnetic resonance imaging apparatus and a floor, which platform has a base plate and an upper magnetic resonance imaging apparatus supporting plate, which upper supporting plate lies over the base plate, rotary and sliding guide means for rotating and sliding the platform being interposed between said two plates such that the platform is rotatable along an annular path coaxial to an axis of the guide forming the curved connection between the patient table and the magnetic imaging apparatus and the upper support plate is slidable relative to the base plate, and
wherein the patient table supporting structure has wheels or rollers for sliding the patient table relative to the magnetic resonance imaging apparatus.

2. The system of claim 1, comprising two or more patient tables that can be simultaneously coupled to the magnetic resonance imaging apparatus and moved in different positions relative thereto.

3. The system of claim 2, wherein the guide further includes a plurality of guide means for displacement of each of the two or more tables relative to each other and to the magnetic resonance imaging apparatus.

4. The system of claim 3, wherein the guide means comprises an arched guide and each table being connected to a carriage that can be coupled to said removable connection, wherein the tables have a supporting structure with wheels or rollers sliding.

5. The system of claim 1, wherein the patient table supporting structure is also disposed on the platform interposed between the magnetic resonance imaging apparatus and the floor.

6. The system of claim 1, wherein the rotary and sliding guide means interposed between the base plate and the upper plate of the platform is oriented along at least one straight axis.

7. The system of claim 1, wherein the guide of the curved connection includes a table sliding guide that has the shape of a sector of a circle, whose axis is oriented perpendicular to the floor or to the apparatus supporting surface.

8. The system of claim 7, wherein the rotary and sliding guide means between the base plate and the upper supporting plate of the platform for the magnetic resonance imaging apparatus also has the shape of a sector of a circle and is coaxial to the table sliding guide.

9. The system of claim 7, wherein the platform has an annular shape, opposite sides of the magnetic resonance imaging apparatus having slidable support elements which rest directly on the platform, and the table supporting structure lies directly on the platform, which table supporting structure has elements for sliding on the floor.

10. The system of claim 5, wherein the platform also partly extends beneath the table, coincident with at least the portion of the table supporting structure at the side whereat the table is coupled to the magnetic resonance imaging apparatus sliding guide.

11. The system of claim 10, wherein the portion of the platform which supports at least partly the table extends flush with the upper supporting surface of the portion of the sliding platform which supports the magnetic resonance imaging apparatus.

12. The system of claim 11, wherein the portion of the platform which supports the table is stationary and the table supporting structure has means for sliding or rolling on said portion of the platform.

13. The system of claim 11, wherein the portion of the platform which supports the table has an upper table supporting plate which is slidable along a base plate, whose extension is shaped like a sector of a circle coaxial to the sector shaped sliding guide between the upper support plate and the base part of the platform portion supporting the magnetic resonance imaging apparatus.

14. The system of claim 5, wherein the platform has a magnetic resonance imaging apparatus supporting extension which is designed to also support said apparatus on the side(s) thereof that are not fitted with the table sliding guide.

15. The system of claim 7, wherein at least one side of the cavity forms an extension of the patient supporting surface of the patient table.

16. The system of claim 15, wherein the sector-shaped sliding guides for the table and/or the upper support plate of the magnetic resonance imaging apparatus supporting platform and/or the upper support plate of the extension of said platform, for supporting at least a portion of the table are coaxial to each other, their axis being perpendicular to and intersecting said at least one side of the magnet structure that forms the extension of the patient supporting surface of the table.

17. The system of claim 1, wherein the cavity is open on two parallel sides.

18. The system of claim 1, wherein the magnet structure has three open sides, the three open sides include two opposite parallel sides and one side transverse thereto, and the magnet structure substantially has a C or U shape.

19. The system of claim 15, wherein the sector-shaped guide for the table and/or the upper support plate of the magnetic resonance imaging apparatus supporting platform and/or the upper support plate of the extension of said platform, for supporting at least a portion of the table extends through an angle of 360°.

20. The system of claim 15, wherein the sector-shaped guide for the table and/or the upper support plate of the magnetic resonance imaging apparatus supporting platform and/or the upper support plate of the extension of said platform, for supporting at least a portion of the table extends through an angle of less than 360°.

21. The system of claim 15, wherein the sector-shaped guide for the table and/or the upper support plate of the magnetic resonance imaging apparatus supporting platform and/or the upper support plate of the extension of said platform, for supporting at least a portion of the table extends through an angle of less than 180°.

22. The system of claim 5, wherein the platform for supporting the magnetic resonance imaging apparatus and at least a portion of the table is composed of elements having the shape of coaxial annular sectors.

23. The system of claim 1, wherein sides of the magnet structure that form an extension of the table have an outer edge that is arched coaxial to the curved connection, which edge extends along said guide and is superimposed thereto, level with the table surface.

24. The system of claim 2, wherein the guide for relative slidable displacement of at least one of the patient tables and the magnetic resonance imaging apparatus is fitted onto an intermediate table part that may be removably coupled to the magnetic resonance imaging apparatus and has a complementary cavity for accommodating the magnet structure sides which form the extension of the tables, said intermediate part of the tables being common to the two or more tables that may be simultaneously coupled to the magnetic resonance imaging apparatus.

25. The system of claim 24, wherein said intermediate part of the table is coupled to the magnetic resonance imaging apparatus, by means of sliding guides, along which the sliding motion occurs along at least one coupling and uncoupling direction, means being provided for locking said intermediate part of the table in the coupling limit stop position and/or in one or more different intermediate positions marking different distances of the intermediate part of the table from the magnet structure of the magnetic resonance imaging apparatus.

26. The system of claim 7, wherein the table is coupled to the magnetic resonance imaging apparatus at one end side and extends radially with respect to the sector-shaped sliding guide.

27. A system comprising:
a magnetic resonance imaging apparatus; and
two patient tables that are coupled to said apparatus,
a guide for relative slidable displacement of said patient tables and said apparatus, which guide consists of least two diametrically opposite, separate curved sections mounted on opposite sides of the apparatus, which sections extend through an angle of less than 180°,
wherein the two separate guide sections are coaxial to each other and the magnetic resonance imaging apparatus may rotate coaxially to said separate guide sections.

28. The system of claim 27, wherein the two guide sections are diametrically opposite portions of a single continuous sector-shaped guide.

29. The system of claim 27, wherein the magnetic resonance imaging apparatus and/or the tables have wheels or means allowing them to slide or roll on the floor surface and/or on a platform.

30. The system of claim 27, wherein the two tables have means for locking them in the angular positions in which they are coupled to the magnetic resonance imaging apparatus.

31. A system comprising:
a magnetic resonance imaging apparatus; and
at least one patient table or two tables that are coupled to said apparatus, on diametrically opposite sides of a guide for relative slidable displacement of said patient table or tables and said apparatus, which guide has the shape of a sector of a circle, and
at least one platform that rotates with an axis of rotation coaxial to an axis of the sector-shaped guide for the at least one of the tables, the magnetic resonance imaging apparatus being positioned on said platform, whereas the table or tables have means allowing them to slide or roll directly on the floor.

32. The system of claim 31, wherein the platform has a circular shape, further comprising an additional annular platform being provided adjacent and coincident with an area supporting at least a portion of the table supporting structure, which additional platform supports at least a portion of the table supporting structure.

33. The system of claim 32, wherein the annular platform which supports at least a portion of the table structure is also rotatable and coaxial to the platform for supporting the magnetic resonance imaging apparatus and to the axis of the table sliding guide.

34. The system of claim 33, wherein the table supporting structure rests on the rotating additional annular platform in a non slidable manner at one end side, and on the floor or a stationary platform, with the interposition of sliding or rolling means, at the other end side.

* * * * *